United States Patent [19]

Cheung et al.

[11] 4,308,062

[45] Dec. 29, 1981

[54] DENTAL CAVITY VARNISH COMPOSITION

[75] Inventors: Peter P. L. Cheung, Gulph Mills; Barry V. Evangelist, Tredyffrin Township, Chester County, both of Pa.

[73] Assignee: Pennwalt Corporation, Philadelphia, Pa.

[21] Appl. No.: 140,322

[22] Filed: Apr. 14, 1980

[51] Int. Cl.³ .............................................. C09K 3/100
[52] U.S. Cl. ..................................... 106/35; 106/186; 106/195
[58] Field of Search ................. 106/195, 186, 178, 35; 260/998.11; 433/217, 228

[56] References Cited

U.S. PATENT DOCUMENTS 3,087,835  4/1963  Auer ..................................... 106/195
3,265,515  8/1966  Wilhelmsen .......................... 106/193

OTHER PUBLICATIONS

Ibert Mellan "Industrial Plasticizers" 1963, p. 241.

Primary Examiner—Allan Lieberman
Assistant Examiner—P. Short

[57] ABSTRACT

Dental cavity varnish compositions comprising a solution of nitrocellulose and toluene sulfonamide which wet and precisely conform to each "peak" and "valley" of the extensive microundercuts generated during cavity preparation. The varnish compositions are compatible with composite resin restorative materials.

12 Claims, No Drawings

DENTAL CAVITY VARNISH COMPOSITION

STATEMENT OF THE INVENTION

This invention relates to dental cavity varnish compositions which precisely conform to dental cavity walls and are compatible with composite resin restorative materials.

BACKGROUND AND SUMMARY OF THE INVENTION

In the removal of the enamel shell which protects the underlying structure, the more permeable dentin is exposed to thus render the remaining tooth structure more susceptible to dental decay as well as creating an entrance for harmful stimuli to the vital pulp beneath.

A common practice prior to restoring the missing structure with a filling material or cement is to apply a thin layer of cavity varnish over the entire exposed dentin area in order to (1) provide a barrier to moisture penetration, (2) serve as insulation against external stimuli, and (3) reduce marginal leakage around a restoration.

Cavity preparation generates extensive microundercuts throughout the cavity walls. These microundercuts serve to promote good retention of a closely packed restoration. In order to benefit from these microundercuts, a cavity varnish should precisely conform to each "peak" and "valley" of the microundercuts with no concomitant loss of definition thereof caused by the varnish. Thus, the varnish must be capable of fully wetting the dentin surfaces while spreading uniformly over their general topography, and yet not swamping the microundercuts. Conventional cavity varnishes have been only mildly successful in fulfilling the above requirements.

Additionally, a dental cavity varnish should be compatible with composite resin restorative materials, such as bisphenol-A resin, for example, currently in wide usage by the dental profession.

It is well known that composite materials can irritate underlying tooth structures. The use of a protective varnish therefore is appropriate. Unfortunately, traditional varnishes were developed, in the main, for compatible use with amalgams and silicates, both widely used prior to composite resin restorative materials. For example, a widely used prior art copal-containing cavity varnish caused an unpolymerized mushy layer to form when the composite was applied over the varnish film. This unreacted layer permitted ready access to the dentin area, or seepage thereinto, of harmful stimuli.

The present invention substantially satisfies the abovementioned requirements, i.e., complete wetting of the dentin surfaces while providing a thin but uniform film over the microundercuts without obstructing the peaks and valleys thereof; and complete compatibility with composite resin restorative materials, as well as amalgams and silicates. In addition thereto, the present varnish is fast drying, hydrophobic when dry, simple to use, and possesses long shelf life and good sealing ability.

DETAILED DESCRIPTION OF THE INVENTION

The present invention resides in compositions of matter illustrated by the following non-limiting examples tabulated below:

TABLE I

| | EXAMPLES | | | | | |
|---|---|---|---|---|---|---|
| | 1 | 2 | 3 | 4 | 5 | 6 |
| *Nitrocellulose (A), parts | 7.5 | 5.0 | 5.0 | — | — | — |
| *Nitrocellulose (B), parts | — | — | — | 7.0 | — | — |
| *Nitrocellulose (C), parts | — | — | — | — | 6.5 | — |
| **Nitrocellulose (D), parts | — | — | — | — | — | 6.5 |
| Toluene Sulfonamide parts | 3.5 | 5.0 | 5.0 | 4.0 | 4.5 | 4.5 |
| Ethyl Acetate parts | 50.0 | 40.0 | 50.0 | 50.0 | 50.0 | 50.0 |
| Ether parts | 50.0 | 40.0 | 50.0 | 40.0 | 50.0 | 50.0 |
| Ethyl Alcohol parts | — | 20.0 | — | 10.0 | — | — |

*Nitrocellulose (A), (B), and (C), each dissolved in a 25% solution of ethyl alcohol 25%, toluene 55%, and ethyl acetate 20%; the resulting nitrocellulose solutions having viscosities of 3 to 4 seconds, 4 to 5 seconds, and 6 to 8 seconds respectively, in accordance with ASTM D-301-56.
**Nitrocellulose (D) dissolved in a 20% solution, in lieu of the 25% solution abovedescribed, to yield a viscosity of 6 to 8 seconds, in accordance with ASTM D-301-56.

With the solvents of Examples 1 through 6 above tabulated, i.e., ethyl acetate, ether and ethyl alcohol, the effective ranges of the nitrocellulose and toluene sulfonamide were determined to fall between about 3 to 10 parts and 0.5 to 6.0 parts respectively, preferably respectively 5.0 to 7.5 parts and 3.5 to 5.0 parts. Below about 3 parts nitrocellulose, and above about 10 parts nitrocellulose, the resultant varnish film is undesirably thin and thick respectively. Below about 0.5 parts toluene sulfonamide, the varnish fails to spread satisfactorily, whereas above about 6.0 parts, the resultant film is not sufficiently water-repellent.

Nitrocellulose imparts film forming properties to the composition. The resultant film is tough and water-repellant. Toluene sulfonamide is highly compatible with the nitrocellulose and with composite restorative resin materials. It spreads well and assists the cavity varnish composition in wetting the dentin surfaces. In combination, the nitrocellulose and toluene sulfonamide form a sealing film which chemically bonds to the dentin and to the resin or composite restorative while yet satisfying the requirements set forth and described hereinabove.

We claim:
1. A dental cavity varnish composition comprising nitrocellulose in the range between about 5.0 to 7.5 parts, toluene sulfonamide in the range between about 3.5 to 5.0 parts, and 100 parts of a mixture of solvents for said nitrocellulose and toluene sulfonamide.

2. The composition of claim 1 wherein said nitrocellulose is dissolved in a 25% solution comprising ethyl alcohol 25%, toluene 55%, and ethyl acetate 20% to yield a viscosity of nitrocellulose solution of 3 to 4 seconds in accordance with ASTM D-301-56, and said solvent comprises 50 parts each ethyl acetate and ether.

3. The composition of claim 2 wherein said dental cavity varnish composition comprises, by parts; nitrocellulose 7.5, toluene sulfonamide 3.5, ethyl acetate 50 and ether 50.

4. The composition of claim 2 wherein said dental cavity varnish composition comprises, by parts; nitrocellulose 5.0, toluene sulfonamide 5.0, ethyl acetate 50 and ether 50.

5. The composition of claim 1 wherein said nitrocellulose is dissolved in a 25% solution comprising ethyl alcohol 25% toluene 55%, and ethyl acetate 20% to yield a viscosity of nitrocellulose solution of 3 to 4 seconds in accordance with ASTM D-301-56, and said solvent comprises 40 parts each ethyl acetate and ether, and 20 parts ethyl alcohol.

6. The composition of claim 6 wherein said dental cavity varnish composition comprises, by parts: nitrocellulose 5.0, toluene sulfonamide 5.0; and 100 of said solvent.

7. The composition of claim 1 wherein said nitrocellulose is dissolved in a 25% solution comprising ethyl alcohol 25%, toluene 55%, and ethyl acetate 20% to yield a viscosity of nitrocellulose solution of 4 to 5 seconds in accordance with ASTM D-301-56, and said solvent comprises, by parts: ethyl acetate 50, ether 40, and ethyl alcohol 10.

8. The composition of claim 7 wherein said dental cavity varnish composition comprises, by parts; nitrocellulose 7.0, toluene sulfonamide 4.0; and 100 of said solvent.

9. The composition of claim 1 wherein said nitrocellulose is dissolved in a 25% solution comprising ethyl alcohol 25%, toluene 55%, and ethyl acetate 20% to yield a viscosity of nitrocellulose solution of 6 to 8 seconds in accordance with ASTM D-301-56, and said solvent comprises 50 parts each ethyl acetate and ether.

10. The composition of claim 9 wherein said dental cavity varnish composition comprises, by parts: 6.5 nitrocellulose, 4.5 toluene sulfonamide, and 100 of said solvent.

11. The composition of claim 1 wherein said nitrocellulose is dissolved in a 20% solution comprising ethyl alcohol 25%, toluene 55%, and ethyl acetate 20% to yield a viscosity of nitrocellulose solution of 6 to 8 seconds in accordance with ASTM D-301056, and said solvent comprises 50 parts each ethyl acetate and ether.

12. The composition of claim 11 wherein said dental cavity varnish composition comprises, by parts: 6.5 nitrocellulose, 4.5 toluene sulfonamide, and 100 of said solvent.

* * * * *